United States Patent [19]

Kaswan

[11] Patent Number: 4,839,342
[45] Date of Patent: * Jun. 13, 1989

[54] METHOD OF INCREASING TEAR PRODUCTION BY TOPICAL ADMINISTRATION OF CYCLOSPORIN

[75] Inventor: Renee Kaswan, Athens, Ga.

[73] Assignee: University of Georgia Research Foundation, Inc., Athens, Ga.

[*] Notice: The portion of the term of this patent subsequent to Jun. 13, 2006 has been disclaimed.

[21] Appl. No.: 92,466

[22] Filed: Sep. 3, 1987

[51] Int. Cl.$^4$ .............................................. A61K 37/02
[52] U.S. Cl. .................................... 514/11; 514/915
[58] Field of Search ............... 424/78; 514/11, 9, 912, 514/914, 915, 15; 530/317

[56] References Cited

U.S. PATENT DOCUMENTS

| | | | |
|---|---|---|---|
| 4,108,985 | 8/1978 | Ruegger et al. | 514/11 |
| 4,117,118 | 9/1978 | Harri et al. | 514/11 |
| 4,210,581 | 7/1980 | Ruegger et al. | 530/321 |
| 4,215,199 | 7/1980 | Harri et al. | 435/71 |
| 4,220,641 | 9/1980 | Traber et al. | 514/11 |
| 4,220,657 | 9/1980 | Johnson et al. | 514/912 |
| 4,288,431 | 9/1981 | Traber et al. | 514/11 |
| 4,289,851 | 9/1981 | Traber et al. | 435/71 |
| 4,384,996 | 5/1983 | Bollinger et al. | 530/321 |
| 4,388,307 | 6/1983 | Cavanak | 514/11 |
| 4,396,542 | 8/1983 | Wenger | 530/32 |
| 4,452,818 | 6/1984 | Haidt | 514/912 |
| 4,554,351 | 11/1985 | Wenger | 514/11 |
| 4,639,434 | 1/1987 | Wenger et al. | 514/11 |
| 4,649,047 | 3/1987 | Kaswan | 514/11 |
| 4,681,754 | 7/1987 | Siegl | 424/10 |
| 4,703,033 | 10/1987 | Seebach | 514/11 |

FOREIGN PATENT DOCUMENTS

| | | | |
|---|---|---|---|
| 19197 | 3/1972 | Australia | 424/78 |
| 8404681 | 12/1984 | PCT Int'l Appl. | 514/912 |
| 8501875 | 5/1985 | PCT Int'l Appl. | 514/914 |
| 8603966 | 7/1986 | PCT Int'l Appl. | 514/912 |

OTHER PUBLICATIONS

Kaswan et al., Am. J. Vet. Res. 46, 376-383 (1985).
Wenger, Synthesis of Cyclosporin and Analogues, pp. 14-25 in Cyclosporin vol. 1, Grune & Stratton, Inc. (New York, 1983).
BenEzra et al., Amer. J. Ophthalmol. 101, 278-282 (1986).
Hunter et al., Clin. Exp. Immunol. 45, 173-177 (1981).
Boisjoly et al., Arch. Ophthalmol. 102, 1804-1807 (1984).
Mosteller et al., Investigative Ophthalmol. Supp. 25, 3, 38 (1984).
Nussenblat et al., Amer. J. Ophthalmol. 96, 275-282 (1983).
Hoffman, et al., *Kin. Mbl. Augenheilk.* 187, 92-95 (1985) and certified translation thereof.
"Aspirin Therapy in Vernal Conjunctivitis" by Abelson, et al., *Amer. J. Opthal.* 95, 502-505 (1983).
"Cryosurgery in the Management of Vernal Keratoconjunctivitis" by Abiose, et al., *Annals of Ophthal.* 15(8), 744-747 (1983).
"Vernal Conjunctivitis" by Allansmith, Chapter 9, pp. 1-8 *Clinical Opthalmology*, vol 4, (Harper & Row 1986).
"Cyclosporine Eyedrops for the Treatment of Severe Vernal Keratoconjunctivitis" BenEzra, et al. *Amer. J. Opthal.* 101, 278-282 (1986).
"Diagnosis and Treatment of Tear Deficiencies" Lemp, Chapter 14, pp. 1-10.
*Clinical Opthalmology* vol. 4, Duane and Jaeger, Ed. (Harper & Row 1986).
"Diseases of the Cornea" by Grayson at pp. 334-367 (The C.V. Mosby Co. 1983).

Primary Examiner—Delbert R. Phillips
Assistant Examiner—T. D. Wessendorf
Attorney, Agent, or Firm—Kilpatrick & Cody

[57] ABSTRACT

The present invention provides a method of treating an aqueous-deficient dry eye state in a patient suffering therefrom, which method includes the step of administering cyclosporin topically to the patient's eye. The cyclosporin is administered as a solution, suspension or ointment in a pharmaceutically acceptable excipient.

18 Claims, No Drawings

METHOD OF INCREASING TEAR PRODUCTION BY TOPICAL ADMINISTRATION OF CYCLOSPORIN

FIELD OF THE INVENTION

The present invention relates to a method of increasing tear production in a patient suffering from deficient tears in the eye due to an autoimmune dysfunction of the lacrimal (tear) glands. More specifically, this invention relates to a method of treating immune mediated keratoconjunctivitis sicca (KCS or dry eye disease) in a patient suffering therefrom, which method includes administering a cyclosporin topically to the patient's eye.

BACKGROUND OF THE INVENTION

The exposed part of a normal eye is covered by a thin tear film. The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example immunoglobulin A, lysozyme and beta lysin, are known to have bacteriostatic properties.

A sound lacrimal system functions to form and maintain a properly structured, continuous tear film. The lacrimal apparatus consists of the secretory system (the source), the distribution system and the excretory system (the sink). In the secretory system, aqueous tears are supplied by the main and accessory lacrimal glands.

The bulk of the tear film is made of such aqueous tears. The continuous production and drainage of aqueous tear is important in maintaining the corneal and conjunctival epithelium in a moist state, in providing nutrients for epithelial respiration, in supplying bacteriostatic agents and in cleaning the ocular surface by the flushing action of tear movement.

Abnormalities of the tear film include an absolute or partial deficiency in aqueous tear production (keratoconjunctivitis sicca or KCS).

In relatively mild cases, the main symptom of KCS is a foreign body sensation or a mild "scratchiness". This can progress to become a constant, intense burning or irritative sensation which can be debilitating to the patient.

More severe forms progress to the development of filamentary keratitis, a painful condition characterized by the appearance of numerous strands or filaments attached to the corneal surface. Recent evidence suggests that these filaments represent breaks in the continuity of the normal corneal epithelial cells. The shear created by lid motion pulls these filaments, causing pain. Management of this stage of KCS is very difficult.

A frequent complication of KCS is secondary infection. Several breakdowns in the eye's normal defense mechanism seem to occur, presumably attributable to a decrease in the concentration of antibacterial lysozyme in the aqueous tears of a patient suffering from KCS.

Although KCS can develop in the absence of any other overt systemic abnormality, there is a frequent association of KCS with systemic disease. KCS can occur as part of a larger systemic involvement known as Sjogren's syndrome. This classically consists of the triad of dry eyes, dry mouth, and arthritis.

Histologically in KCS (as part of Sjogren's syndrome or in isolation), the initial changes seen in the lacrimal gland are those of focal lymphocytic and plasma cell infiltrates associated with degeneration of glandular tissue. These changes resemble those seen in autoimmune disease in other tissue, giving rise to the speculation that KCS has an autoimmune basis.

Sjogren's syndrome is recognized as an exocrine gland dysfunction. Characteristically, the lacrimal glands show a mononuclear-cell infiltration that ultimately leads to destruction of the glandular structure.

Conventional treatment of KCS is symptomatic.

Normally, aqueous-deficient dry eye states are treated by supplementation of the tears with artificial tear substitutes. However, relief is limited by the retention time of the administered artificial tear solution in the eye. Typically, the effect of an artificial tear solution administered to the eye dissipates within about thirty to forty-five minutes. The effect of such products, while soothing initially, does not last long enough. The patient is inconvenienced by the necessity of repeated administration of the artificial tear solution in the eye as needed to supplement the normal tears. Moreover, such treatment merely acts to alleviate the symptoms of the dry eye state and does not cure any underlying disorders or causes of the dry eye state.

Histologic studies of the lacrimal glands in patients suffering from Sjogren's syndrome have shown some evidence of lacrimal gland inflammation. Such inflammation may simply be due to the normal aging of the patient. It has been suggested that the use of antiinflammatory agents might serve to decrease the glandular inflammation. The systemic use of corticosteroids has been advocated in these conditions. However, the merit of systemic corticosteroids in dry eye states has not been established. In most dry eye cases the hazards of long term use of antiinflammatory agents would seem to outweigh their potential merit.

Surgical procedures have also been suggested in the management of dry eye states. Where there has been significant conjunctival destruction, mucuous membrane transplants have been advocated. It has also been suggested that parotid (saliva) duct transplantation can be useful in the management of dry eyes. However, since surgical alterations to combat dry eye conditions constitute such a drastic remedy and the benefit resulting from these alterations is questionable, these methods are usually used in dry eye patients only as a last resort.

It has also been suggested to administer orally a dilute solution of pilocarpine to stimulate the autonomic nervous system to effect increased aqueous tear production. This method of treatment has not met with universal favor because of the unpleasant side effects of ingested pilocarpine.

Animal models of Sjogren's syndrome have been instrumental in basic ophthalmic research. A Sjogren's-like disease has been found in dogs with systemic lupus erythematosus.

Canine KCS is a common, chronic progressive, and potentially blinding disease. A continuum of corneal and conjunctival lesions ensues from the dry eye state. The cause of KCS in canines is often not identified. Usually, canine KCS is not an isolated ophthalmic disease. It has been speculated in Kaswan et al., Am. J. Vet. Res. 46, 376–383 (1985), that most cases of canine KCS occur via autoimmune mechanisms.

The term autoimmunity is used to indicate immunologic self injury, but not a singular etiology. Autoimmune disease is multifactorial, including hormonal, environmental, and polygenetic factors. A reasonable concept of autoimmune pathogenesis proposes that autoimmunity may arise whenever there exists a state of immunologic imbalance in which B-cell activity is excessive and/or suppressor T-cell activity is diminished.

Cyclosporins are unique immunosuppressive agents derived from an extract of soil fungi. Cyclosporine (Cyclosporin A) and its natural and synthetic analogs and isomers (such as Cyclosporins B, C, D, E and H) are cyclic peptides composed of 11 amino acid residues. Wenger, *Synthesis of Cyclosporine and Analogues*, pp. 14-25 in *Cyclosporine* vol. 1, Grune & Stratton, Inc. (New York 1983). Cyclosporin A was first proposed for use as an antifungal agent, but its immunosuppressive effects were found to be more marked than its antifungal potential. This drug inhibits the generation of effector T-lymphocytes without inhibiting the expression of suppressor lymphocytes.

Cyclosporine's immunosuppressive properties have led to its use in immune system related diseases. For example, U.S. Pat. No. 4,649,047, the disclosure of which is herein incorporated by reference, describes a method for the treatment of phacoanaphylactic endophthalmitis and uveitis in the anterior or posterior segment of an eye, in which method a cyclosporin is topically administered to the eye. In other ophthalmic applications, cyclosporine has been used topically only for the treatment of external (e.g., corneal) eye diseases.

BenEzra et al., Amer. J. Ophthalmol. 101, 278-282 (1986), describe the effect of 2% cyclosporine eyedrops on severe vernal keratoconjunctivitis. Severe vernal keratoconjunctivitis is a seasonal allergic disorder unrelated to tear deficiency.

Hunter et al., Clin. Exp. Immunol. 45, 173-177 (1981) describe the topical administration of cyclosporine in a rabbit model of corneal graft rejection with positive results. These effects were found to be attributable to T-cell suppression within the eye or within systemic compartments such as blood or lymph.

Boisjoly et al., Arch. Ophthalmol. 102, 1804-1807 (1984), have reported that topical application of cyclosporine had a beneficial prophylactic effect towards the treatment of severe herpetic stromal keratitis.

Mosteller et al., Investigative Ophthalmol. Supp. 25, 3, 38 (1984), propose the potential suppression of deleterious ocular immune reactions such as the eye surface cornea allograft reaction by applying a single dose of a 10% Cyclosporin A ointment in the lower cul-de-sac of rabbit eyelids.

In other ophthalmic applications, where the disease being treated is not limited to the eye surface, cyclosporine has been used systemically.

For example, Nussenblatt et al., Amer. J. Ophthalmol. 96, 275-282 (1983), have reported clinical improvement in some patients with noninfectious posterior uveitis following systemic treatment with cyclosporin.

However, systemic therapy with cyclosporine has serious drawbacks. There is a high risk of adverse responses when cyclosporine is used systemically. Cyclosporine used systemically has been associated with a high incidence of renal toxicity (kidney failure), some cases of hepatotoxicity, increased incidence of lymphoid tumors and increased incidence of opportunistic infections. Cyclosporine is only slightly less toxic than other immunosuppressive agents such as cytoxan or aziothioprine. The systemic side effects of cyclosporine are so severe and so common that they limit its use to life-threatening or in some cases severe sight-threatening disease. Finally, systemic application of cyclosporine is limited by its prohibitive cost.

To date, there has been no suggestion to treat a glandular dysfunction, a lacrimal gland dysfunction or an aqueous-deficient dry eye state with a cyclosporin, either topically or systemically.

It can thus be readily appreciated that provision of a method of increasing tear production in a patient suffering from deficient tears in the eye due to an autoimmune dysfunction of the lacrimal glands, which method provides improved treatment of KCS and eliminates the previously discussed problems, would be a highly desirable advance over the current state of the art in KCS treatment.

OBJECTS OF THE INVENTION

It is therefore an object of this invention to provide a method of increasing tear production for a tear-deficient eye.

It is a second object of this invention to provide a method of increasing tear production in an eye of a patient suffering from an immune mediated dysfunction of the lacrimal glands.

It is an additional object of this invention to provide a method of treating KCS in a patient suffering therefrom.

It is also an object of this invention to provide a method of treating a disorder caused by excessive immune activity in a lacrimal gland of a patient.

It is a further object of this invention to provide a method of treating a disorder exacerbated by KCS in a patient suffering therefrom.

It is another object of this invention to provide a cyclosporin-based treatment of the lacrimal glands without the accompanying adverse physiological responses and economic difficulties associated with systemic cyclosporin treatments.

These and other objects and advantages of the present invention will become more readily apparent after consideration of the following.

STATEMENT OF THE INVENTION

In one aspect, the present invention is directed to a method of treating a dry eye state in a patient by administering a cyclosporin topically to the patient's eye.

In another of its aspects, the present invention provides a cyclosporin-based treatment of an autoimmune dysfunction of the lacrimal glands.

In still another of its aspects, the present invention relates to a cyclosporin in a carrier adaptable to topical administration into a patient's eye.

DESCRIPTION OF PREFERRED EMBODIMENTS

The present invention, as well as other objects and features thereof, will be understood more clearly and fully from the following description of certain preferred embodiments.

The present invention provides a method of treating an aqueous-deficient dry eye state due to an autoimmune dysfunction of the lacrimal glands in a patient suffering therefrom, which method includes the step of administering a cyclosporin topically to the patient's eye. Surprisingly, this topical administration of a cyclosporin to the eye provides cyclosporin treatment to the lacrimal glands, and such treatment increases tear production in a patient suffering from KCS.

Conventional treatment of KCS involves alleviating the symptoms of the dry eye state without treating the underlying disorders or causes of the dry eye state. Symptomatic treatment of the dry eye state, such as by supplementation of the aqueous tears with artificial tear substitutes, necessarily involves continuous and repeated attention as needed to alleviate the recurring symptoms.

To date, there has been no suggestion to treat a glandular dysfunction, a lacrimal gland dysfunction or an aqueous-deficient dry eye state with a cyclosporin, either topically or systemically.

Topical administration to a patient's eye has surprisingly been found to be an excellent method for providing a cyclosporin to the lacrimal glands of the patient to treat KCS. Additionally, since by its very nature topical administration does not require cyclosporin dispersion throughout the patient's system as is the case with systemic administrations, the present invention provides a means for directing cyclosporin to the desired location without the accompanying high risk of adverse responses and high cost associated with systemic treatments.

Cyclosporine concentration was determined for various eye compartments and tissues surrounding the eye after bilateral topical administration of cyclosporine to the eyes of three rabbits. The cyclosporine was administered in each of the rabbits' eyes in drops (approximately 17 microliters) of 2% radiolabelled cyclosporine in an olive oil solution applied every 15 minutes for 6 applications, followed by a period of two hours to allow for absorption. The rabbits were then euthanized and the eyes and surrounding tissue were enucleated and frozen. The eyes and surrounding tissue were dissected into their component parts. These were then digested in collagenase and the resulting solutions were analyzed by liquid scintillation counting for cyclosporine content. The following average cyclosporine concentrations were measured:

Accessory lacrimal gland: 2850 mg of cyclosporine/gram of tissue;
Periorbital fat: 800 ng/gram;
Cornea: 4700 ng/gram;
Iris: 1200 ng/gram;
Retina: 50 ng/gram;
Aqueous humor: 30 ng/gram;
Vitreous humor: 30 ng/gram;
Anterior sclera: 3150 ng/gram; and
Posterior sclera: 1550 ng/gram.

Thus, topical administration of cyclosporine to a patient's eye surprisingly provides a suitable concentration of cyclosporine to the lacrimal glands of the patient for treatment of KCS.

In accordance with the present invention, the cyclosporin may be used in any efficacious concentration, e.g., 0.01 to saturation (e.g., greater than 20 weight percent), in a pharmaceutically acceptable excipient. From 0.01 to 50 weight percent, preferably from 0.1 to 20 weight percent, of a cyclosporin in a pharmaceutically acceptable excipient is used. Such pharmaceutically acceptable excipients are, for example, animal oil, vegetable oil, an appropriate organic or aqueous solvent, an artificial tear solution, a natural or synthetic polymer or an appropriate membrane.

Examples of these pharmaceutically acceptable excipients are olive oil, arachis oil, castor oil, mineral oil, petroleum jelly, dimethyl sulphoxide, chremophor, Miglyol 182 (commercially available from Dynamit Nobel Kay-Fries Chemical Company, Mont Vale, N.J.), an alcohol (e.g., ethanol, n-propyl alcohol or iso-propyl alcohol), liposomes or liposome-like products or a silicone fluid. Preferred excipients are dimethyl sulphoxide and olive oil. Mixtures of at least two of any suitable excipients may be used.

Examples of artificial tear excipients which can be advantageously used in the practice of this invention are isotonic sodium chloride, cellulose ethers such as hydroxypropylmethylcellulose and hydroxyethylcellulose, polyvinyl alcohol and other commercially available artificial tea solutions.

An example of useful polymeric excipient is a polyoxyethylated castor oil.

Examples of pharmaceutically acceptable membranes which can advantageously be used in the practice of this invention are: microdone, an artificial lipid membrane, polyvinylalcohol, or methylcellulose.

The cyclosporin is advantageously administered topically as an ophthalmic drop (solution or suspension) or ophthalmic ointment containing a effective amount of the cyclosporin. Concentrations of 0.01 to 50 weight percent, preferably 0.1 to 20 weight percent, of a cyclosporin are used.

In accordance with the method of the present invention, a cyclosporin is administered topically in any quantity required to provide the degree of treatment needed. For example, 5 microliters to 1 milliliter of a solution, suspension or ointment containing an effective amount of a cyclosporin, such as 0.01 to 50 weight percent, preferably 0.1 to 20 weight percent, of cyclosporin is advantageously used.

Cyclosporins which are useful in the practice of the present invention are both natural or synthetic cyclosporin. For example, Cyclosporin A is advantageously used in the practice of the present invention. Other forms of cyclosporins (e.g., analogs and isomers such as Cyclosporins B, C, D, E, and H) may also be used. Mixtures of at least two different cyclosporins may be used.

Numerous advantages accrue with the practice of the present invention. The method of the present invention is useful in that it can locally prevent activation of a presystemic response. Topical administration of a cyclosporin into a patient's tear deficient eye increases tear production in the eye. Thus, such treatment further serves to correct corneal and conjunctival disorders exacerbated by tear deficiency and KCS, such as corneal scarring, corneal ulceration, inflammation of the cornea or conjunctiva, filamentary keratitis, mucopurulent discharge and vascularization of the cornea. Furthermore, cyclosporin directly decreases the immune response of granulation and neovascularization in the cornea.

Further objects of this invention, together with additional features contributing thereto and advantages accruing therefrom, will be apparent from the following examples of the invention.

EXAMPLE 1

A one year old standard female Poodle with conjunctivitis exhibited mild aqueous tear deficiency in both eyes. The dog had a Schirmer tear test value of 15 mm/minute in the right eye and 10 mm/minute in the left eye.

The Schirmer tear test is a test of aqueous tear production. The test depends upon observing the extent of wetting of a strip of filter paper placed over the lower lid of an eye for a specified time. Standardized strips are commercially available. The strip is folded at a notched marking and is then placed over the edge of the lateral one-third of the eyelid. The strip is usually left in place for a period of time while the patient looks straight ahead in dim light.

The degree of wetting of the paper is measured in mm from the notch. For human patients, a normal end point is 5 mm of wetting at five minutes. For canine patients, the normal tear production is 14 to 20 mm. of wetting at one minute.

The dog was treated with dexamethasone by topical administration in both eyes four times daily.

The same dog at approximately six years old still exhibited conjunctivitis in both eyes and had a Schirmer tear test value of 3 mm/minute in both eyes. Topical dexamethasone was used in both eyes twice daily for nine weeks without benefit.

The dog was then treated by topical application of 2% cyclosporine in an olive oil solution in both eyes once daily without any other medications. After ten days, the dog showed markedly increased tear production and had a Schirmer tear test value of 22 mm/minute in the right eye and 8 mm/minute in the left eye.

The treatment by topical application of 2% cyclosporine in an olive oil solution in both eyes once daily was continued for an additional three weeks. At this time, the dog exhibited plentiful aqueous tear production and the treatment was stopped for one week. After this week, the dog had a Schirmer tear test value of 10 mm/minute in the right eye and 9 mm/minute in the left eye.

At this time, the treatment by topical application of 2% cyclosporine in an olive oil solution in both eyes once daily was restarted and continued for six days. After these six days, the dog had a Schirmer tear test value of 22 mm/minute in the right eye and 16 mm/minute in the left eye.

In this case, a dog with chronic tear deficiency in which prior use of corticosteroids failed to improve tear secretion showed a surprising increase in tear production with cyclosporine treatment. The increased tear production continued only while cyclosporine therapy continued. When the treatment was stopped for a week, recurrence of tear deficiency was found. However, tear production increased to normal levels after the treatment was restarted.

EXAMPLE 2

An eight year old male Lhasa Apso had had a four year prior cat scratch in his left eye and an active 4 mm stromal ulcer in his right eye. An ocular examination of the dog showed conjunctivitis in both eyes with mucopurulent discharge, diffuse irregular corneal surfaces, pigment formation and neovascularization in the cornea of the left eye. The Schirmer tear test values were 12 mm/minute in the right eye and 3 mm/minute in the left eye.

The dog was treated with topical administration to both eyes of 2% cyclosporine in an olive oil solution once daily, neosporin twice daily and ophthalmic petrolatum. After five days, the Schirmer tear test values were 22 mm/minute in the right eye and 23 mm/minute in the left eye. In addition, the ulcer in the right eye was healed to 2 mm and the left eye was assessed to have decreased vascularization.

In this case, cyclosporine increased tear production significantly in a short period of time. Moreover, cyclosporine, unlike corticosteroids, did not retard corneal healing nor activate corneal collagenase. Accordingly, cyclosporine can be used in eyes having active corneal ulcers.

EXAMPLE 3

A six year old male English Bulldog had had a long history of KCS. The Schirmer tear test values were 2 mm/minute in the right eye and 3 mm/minute in the left eye.

The right eye was neovascularized over the entire cornea. No intraocular detail could be visualized through the opaque cornea. The cornea was grossly thick and irregular in surface. The left eye had neovascularization over about half of the cornea, mostly axially.

The dog was treated with three drops of 2% pilocarpine by mouth. After two hours, the Schirmer tear test values were 0 mm/minute in the right eye and 10 mm/minute in the left eye.

The dog was then treated with 2% cyclosporine in an olive oil solution administered topically to both eyes once daily and three drops of 2% pilocarpine administered by mouth twice daily. After twelve days, the Schirmer tear test values were 10 mm/minute in the right eye and 15 mm/minute in the left eye.

In this case, while pilocarpine alone increased tear production in the left eye from a Schirmer tear test value of 3 mm/minute to 10 mm/minute, pilocarpine did not increase tear production in the right eye. Use of cyclosporine with pilocarpine increased tear production to a Schirmer tear test value of 15 mm/minute in the left eye and from 0 mm/minute to 10 mm/minute in the right eye. The use of cyclosporine markedly increased tear production over the use of pilocarpine alone.

EXAMPLE 4

A seven year old Miniature Poodle had a history of severe KCS of six to seven months duration. The dog was considered to be blind for two months duration. Treatment with artificial tears six times daily did not effect the apparent blindness.

The dog showed marked mucopurulent discharge in both eyes. The Schirmer tear test values were 0 mm/minute in both eyes. The dog's corneas were thickened and neovascularized with an irregular surface. No intraocular detail could be visualized through the opaque corneas.

The dog was treated with one drop of 2% pilocarpine by mouth two times daily and ophthalmic petrolatum four times daily. After two weeks, the Schirmer tear test values were still 0 mm/minute in both eyes. The corneal vascularity and scarring remained dense and the anterior chambers of the dog's eye were not visualizable.

The dog was then treated with 2% cyclosporine in an olive oil solution administered topically in both eyes once daily and two drops pilocarpine administered by mouth twice daily.

After two weeks, the Schirmer tear test values were 8 mm/minute in the right eye and 6 mm/minute in the left eye. Although corneal vascularization and scarring remained, the iris and lens could be evaluated, there was no mucoid discharge in either eye as previously and the KCS was assessed as medically improved.

After similar treatment for another two months, the Schirmer tear test values were 11 mm/minute in the right eye and 17 mm/minute in the left eye. The dog's eyes had minimal corneal vascularization and minimal scarring.

In this case, although the dog was treated initially with pilocarpine, pilocarpine alone is not known to cause such a drastic improvement in tear production. After treatment with cyclosporine, the dog improved from no tear flow in either eye to normal tear production in both eyes. The dog improved from blinding corneal inflammation to very mild corneal pigmentation in both eyes. Treatment with cyclosporine markedly increased tear production and allowed the dog to return to normal vision.

I claim:

1. A method for enhancing or restoring lacrimal gland tearing comprising topically administering cyclosporin to the eye in a pharmaceutically acceptable vehicle.

2. The method of claim 1 for increasing tear production in a tear-deficient eye comprising topically administering a therapeutically effective amount of a cyclosporin to said eye.

3. The method of claim 2 wherein said cyclosporin is administered as a solution, suspension or ointment comprising 0.01 to 50 weight percent of cyclosporin in a pharmaceutically acceptable excipient.

4. The method of claim 3 wherein said cyclosporin is administered in an amount of 0.1 to 20 weight percent.

5. The method of claim 3 wherein the pharmaceutically acceptable excipient is olive oil, arachis oil, castor oil, polyoxyethylated castor oil, mineral oil, petroleum jelly, dimethyl sulphoxide, an alcohol, liposome, silicone fluid or a mixture thereof.

6. The method of claim 2, wherein said cyclosporin is Cyclosporin A.

7. The method of claim 2 for increasing tear production in an eye of a patient suffering from an autoimmune dysfunction of the lacrimal glands comprising administering a therapeutically effective amount of a cyclosporin topically to the patient's eye.

8. The method of claim 2 for treating keratoconjunctivitis sicca in a patient comprising the step of administering a therapeutically effective amount of a cyclosporin topically to the patient's eye.

9. The method of claim 1 for treating a disorder caused by immune activity in a lacrimal gland of a patient comprising the step of topically administering to the patient's eye a therapeutically effective amount of a cyclosporin to enhance or restore tearing.

10. The method of claim 9 wherein said cyclosporin is administered as a solution, suspension or ointment comprising 0.01 to 50 weight percent of cyclosporin in a pharmaceutically acceptable excipient.

11. The method of claim 10 wherein said cyclosporin is administered in an amount of 0.1 to 20 weight percent.

12. The method of claim 10 wherein the pharmaceutically acceptable excipient is olive oil, arachis oil, castor oil, polyoxyethylated castor oil, mineral oil, petroleum jelly, dimethyl sulphoxide, an alcohol, liposome, silicone fluid or a mixture thereof.

13. The method of claim 9, wherein said cyclosporin is Cyclosporin A.

14. The method of claim 1 for treating a disorder exacerbated by deficient tear production in a patient comprising topically administering a therapeutically effective amount of a cyclosporin to the patient's eye to enhance or restore tearing.

15. The method of claim 14 wherein said cyclosporin is administered as a solution, suspension or ointment comprising 0.01 to 50 weight percent of cyclosporin in a pharmaceutically acceptable excipient.

16. The method of claim 15 wherein said cyclosporin is administered in an amount of 0.1 to 20 weight percent.

17. The method of claim 15 wherein the pharmaceutically acceptable excipient is olive oil, arachis oil, castor oil, polyoxyethylated castor oil, mineral oil, petroleum jelly, dimethyl sulphoxide, an alcohol, liposome, silicone fluid or a mixture thereof.

18. The method of claim 14, wherein said cyclosporin is Cyclosporin A.

* * * * *

UNITED STATES PATENT AND TRADEMARK OFFICE
CERTIFICATE OF CORRECTION

PATENT NO. : 4,839,342
DATED : June 13, 1989
INVENTOR(S) : Renee KASWAN

It is certified that error appears in the above-indentified patent and that said Letters Patent is hereby corrected as shown below:

On title page, delete the statement that reads:
"The portion of the term of this patent subsequent to Jun. 13, 2006 has been disclaimed."

Signed and Sealed this

Twenty-sixth Day of March, 1996

Attest:

BRUCE LEHMAN

Attesting Officer

Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   4,839,342

ISSUED          :   June 13, 1989

INVENTOR(S)     :   Renee Kaswan

PATENT OWNER    :   Georgia Research Foundation, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

700 days from the original expiration date of the patent, September 2, 2007, with all rights pertaining thereto as provided by 35 U.S.C. § 156(b).

I have caused the seal of the Patent and Trademark Office to be affixed this 4th day of April 1997.

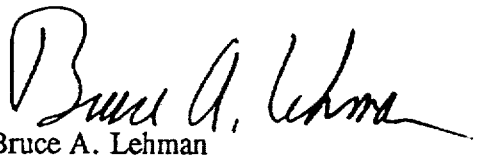

Bruce A. Lehman
Assistant Secretary of Commerce and
  Commissioner of Patents and Trademarks